United States Patent [19]

Schneider et al.

[11] Patent Number: 4,915,957
[45] Date of Patent: Apr. 10, 1990

[54] ANTACID MATERIAL

[75] Inventors: Michael Schneider; Adolf Knecht, both of Freiburg, Fed. Rep. of Germany

[73] Assignee: Gödecke Aktiengesellschaft, Berlin, Fed. Rep. of Germany

[21] Appl. No.: 638,829

[22] Filed: Aug. 8, 1984

Related U.S. Application Data

[63] Continuation-in-part of Ser. No. 513,136, Jul. 12, 1983, Pat. No. 4,482,542, which is a continuation of Ser. No. 260,859, May 6, 1981, abandoned.

[51] Int. Cl.$^4$ ............................................. A61K 33/08
[52] U.S. Cl. ..................................... 424/690; 424/692
[58] Field of Search ........................................... 424/157

[56] References Cited

U.S. PATENT DOCUMENTS

| | | | |
|---|---|---|---|
| 2,923,660 | 2/1960 | Hallmann | 424/157 |
| 3,857,938 | 12/1974 | Rovati et al. | 424/156 |
| 4,105,579 | 8/1978 | Glasscock | 252/317 |

FOREIGN PATENT DOCUMENTS 49-38997  10/1974  Japan ................................. 424/157

OTHER PUBLICATIONS

*Chemical Abstracts*, 83 84853e, 1975.

Primary Examiner—Frederick E. Waddell
Attorney, Agent, or Firm—Francis J. Tinney

[57] ABSTRACT

A process for the preparation of an antacid material prepared from magnesium aluminum hydroxide, wherein magnesium hydroxide and/or magnesium oxide is reacted in an atomic ratio of magnesium to aluminum of 1:1 to 3:1 with an aqueous solution of aluminum sulfate until the pH of the reaction mixture is from 4.0 to 8.0, whereafter water-soluble components are removed from the mixture is known manner and this is isolated and, if desired, dried is described as well as a new embodiment of the formula $[Mg_5Al_{10}(OH)_{26}O_5]$-$(SO_4)_2 \cdot nH_2O$. Also described are pharmaceutical compositions containing such antacid material, in admixture with a conventional pharmaceutical adjuvant, and a method of combating hyperacidity and gastrointestinal diseases, which comprises administering such antacid material.

14 Claims, 6 Drawing Sheets

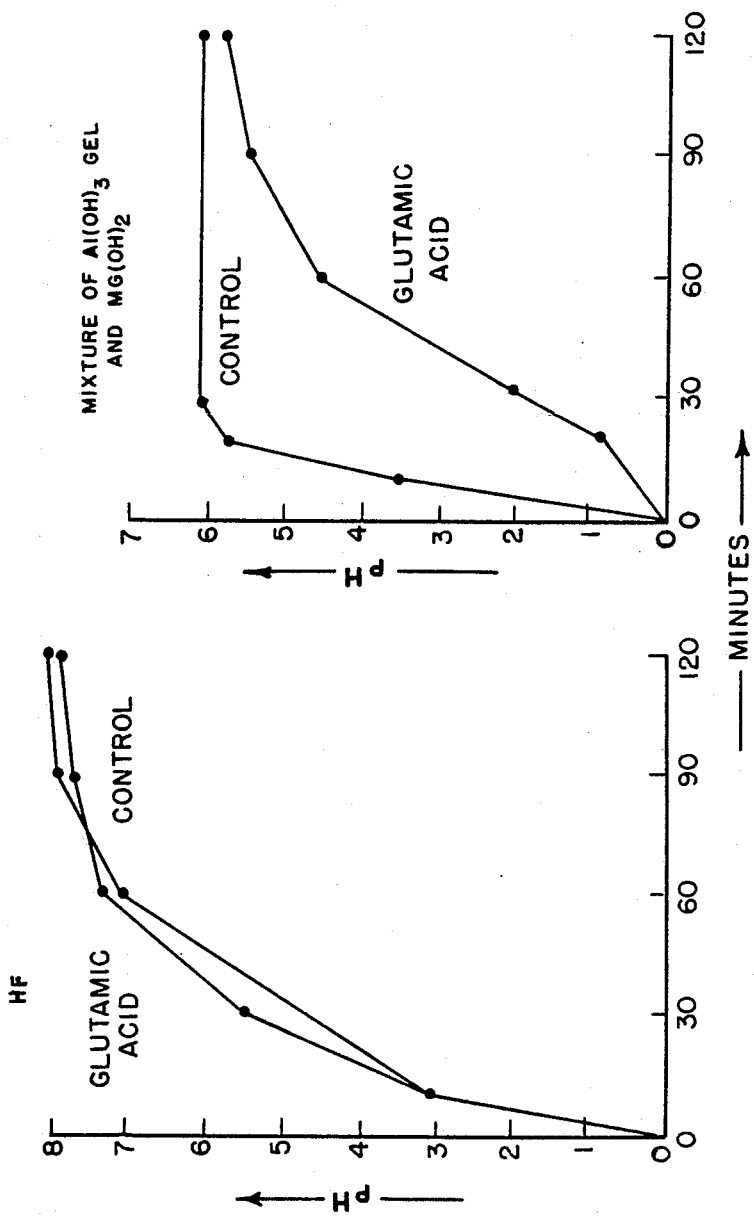

ANTACID MATERIAL

CROSS-REFERENCE TO RELATED APPLICATIONS

This is a continuation-in-part of application Ser. No. 513,136, filed July 12, 1983, now U.S. Pat. No. 4,482,542, which is a continuation of application Ser. No. 260,859, filed May 6, 1981, now abandoned.

BACKGROUND OF THE INVENTION

The present invention is concerned with an antacid material prepared from magnesium oxide/hydroxide and aluminum sulfate and with the preparation thereof.

Aluminum and magnesium hydroxides, especially in gel form, have proved to be effective antacids in the treatment of gastric hyperacidity and of ulcers.

However, the preparation of a practically useful antacid based upon aluminum magnesium hydroxide comes up against considerable difficulties since a large variety of influences have a negative effect upon the effectiveness or compatibility. An excess, in the physiological sense, of magnesium hydroxide, for example, gives rise not only to a rapid increase of the pH value of the gastric juice above the neutral point and thus induces a rebound effect, i.e. a really excessive production of acid, but also exerts a strongly laxative action. An excess of aluminum hydroxide, on the other hand, usually gives rise to undesirable constipation.

In the case of conventional precipitation methods bases, for example sodium hydroxide, are also employed, the cations of which cannot be completely removed from the voluminous gels by washing out and, consequently, these cations manifest their own undesired actions. However, sodium ions in particular must not be present in cases of high blood pressure and of diseases of the kidney and heart.

Because of the harmful effects of sodium ions, an attempt has been made, according to U.S. Pat. No. 4,105,579, to obtain aluminum hydroxide gel in pure form by precipitation from aluminum salts with an aqueous solution of magnesium carbonate and subsequent filtration. In this manner, it is admittedly possible to obtain a sodium-free aluminum hydroxide gel but, for the above-mentioned reasons, it cannot be used directly as an antacid but must be admixed with a proportion of magnesium hydroxide.

According to Federal Republic of Germany Patent Specification No. 2,327,768, aqueous ammonia is used as a precipitation agent for the preparation of aluminum hydroxide. However, this process only apparently solves the problem since ammonium ions are also physiologically undesirable and, in the same way as alkali metal ions, are stubbornly held by the gel.

As is also known from Federal Republic of Germany Patent Specification No. 1,617,277 (column 2, lines 55-63), it is extremely difficult to dry aluminum and magnesium hydroxide gels without losing a considerable part of acid-binding activity. In the case of aluminum hydroxide gels, this disadvantage is even regarded as being a characteristic.

It is an object of the present invention to provide an antacid material which, apart from aluminum and magnesium, contains no other cations and, in a dry state, even after comparatively prolonged storage, does not lose its acid-binding buffering capacity and which has an unusually long period of action, without deviating from the ideal buffer zone of from about pH 3 to pH 5 at any time during the treatment therewith.

This object is, surprisingly, achieved by using solid magnesium hydroxide and/or magnesium oxide for precipitating an antacid from an aqueous solution of aluminum sulfate $[Al_2(SO_4)_3]$, the product obtained, after the removal of water-soluble components, being isolated in known manner and, if desired, dried.

The starting materials are used in an atomic ratio of magnesium to aluminum of 1:1 to 3:1 and preferably to 1.3:1 to 2:1.

The precipitation reaction is finished when the reaction mixture has reached a pH value of from 4.0 to 8.0 and preferably of from pH 5.0 to pH 8.0.

According to U.S. Pat. No. 3,239,416, an attempt has already been made to react a basic aluminum chloride $[Al_2(OH)_2Cl_4$ or $Al_2(OH)_5Cl]$ with appropriate non-toxic alkaline earth metal compounds. However, due to the presence of hydroxyl groups in the aluminum complex, a cross-linking in the end product is only partly possible. Consequently, a gel-like precipitate, a so-called co-gel, is obtained, the properties of which differ considerably from those of the end product obtained according to the present invention and which, in addition, must be freed from undesired chloride ions by repeated and laborious washing. Furthermore, in order to achieve a suitable pH value for the reaction, the addition of sodium carbonate or sodium bicarbonate is usually necessary when carrying out this known process.

A similar proposal, which by-passes the object of the present invention, has also been disclosed in Chemical Abstracts, 83, 84853E (1975). In this case, too, a pre-hydrolysed polybasic aluminum sulfate of limited reactivity is reacted with magnesium hydroxide. Due to the hydrolysis of sodium bicarbonate, undesired sodium ions are entrained which can scarcely be removed from the resultant gel.

In U.S. Pat. No. 4,105,579, a process is described for the preparation of a more or less pure aluminum hydroxide by precipitation from aluminum chloride solutions (or, alternatively, also nitrate and sulfate) by means of an alkaline earth metal carbonate, undesired amounts of carbonate thereby getting into the end product.

SUMMARY OF THE INVENTION

Accordingly, the present invention provides a process for the preparation of an antacid material, wherein magnesium hydroxide and/or magnesium oxide is reacted in an atomic ratio of magnesium to aluminum of 1:1 to 3:1 with an aqueous solution of aluminum sulfate until the pH of the reaction mixture is from 4.0 to 8.0, whereafter water-soluble components are removed from the mixture in known manner and this is isolated and, if desired, dried.

Another aspect of the present invention is an antacid pharmaceutical composition comprising an effective amount of an antacid material prepared from magnesium hydroxide or magnesium oxide and aluminum sulfate in an atomic ratio of magnesium to aluminum of 1:1 to 3:1 in admixture with a conventional pharmaceutical adjuvant.

Still another aspect of the present invention is a method of treating hyperacidity and gastrointestinal diseases, which comprises administering to a mammal suffering therefrom an effective amount of an antacid material in the form of the above pharmaceutical composition.

A preferred embodiment of the invention is an antacid material of the formula $[Mg_5Al_{10}(OH)_{26}O_5](SO_4)_2 \cdot nH_2O$, wherein n is 35–95, preferably 45–85, and, particularly 63, an antacid pharmaceutical composition therewith and a method of treating hyperacidity and gastrointestinal diseases by administering to a mammal suffering therefrom an effective amount of a pharmaceutical composition thereof

BRIEF DESCRIPTION OF THE DRAWINGS

FIG. 2 shows the acid-binding capacity of the product of Example 1 at a dosage of 3 g and 4.5 g of dry substance. It can be seen that, after about 15 minutes, a very flat pH maximum of about pH 4.4 is reached which, after a further 15 minutes, runs practically in a straight line. A distinct pH drop can only be seen after about 130 or 180 minutes.

FIG. 3 shows a comparative curve of the product according to Example 1 from which it can be seen that a product stored for three months shows only a slight loss of activity.

FIG. 4 shows the course of the curve of the acid-binding capacity of a conventional mixture consisting of 5 mMol magnesium hydroxide and 20 mMol aluminum hydroxide gel. The undesired pH maximum can be clearly seen and, in the case of the preparation which is 24 hours old, the pH of 5 is exceeded after only 5 minutes. It can also be seen that the pH value drops again to below 3 in less than an hour.

FIG. 6 illustrates the acid-neutralizing capacity of Antacid HF (product of Example 5) in the presence of control gastric juice and the gastric juice of a fasted stomach (glutamic acid) and that of a comparison mixture.

DETAILED DESCRIPTION

Figure 1:
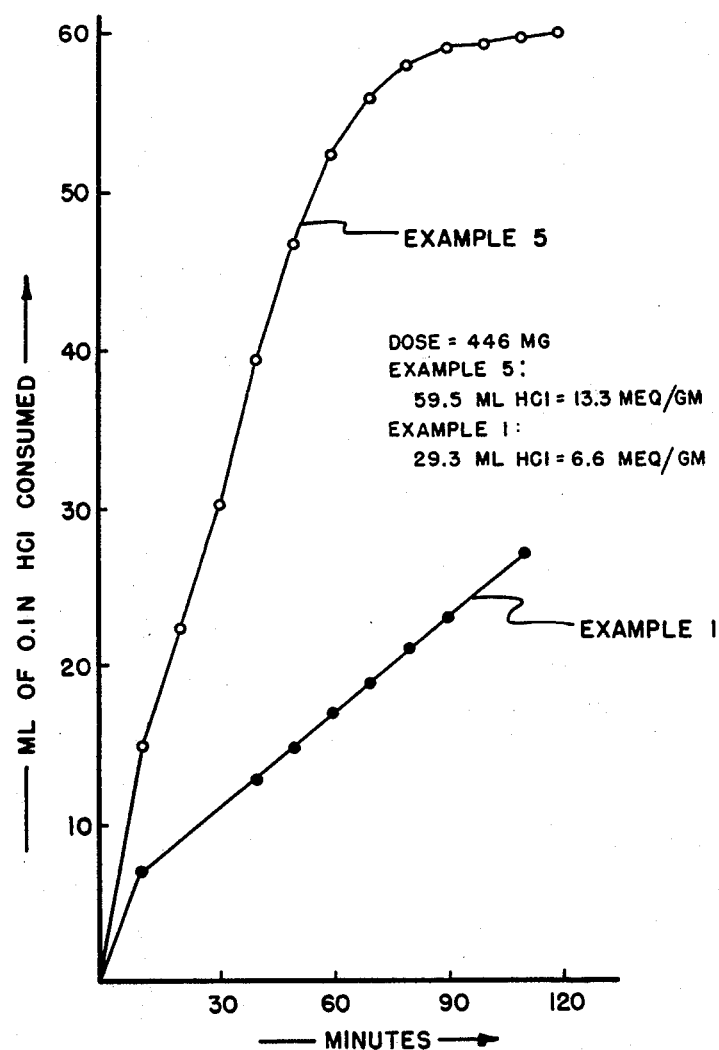
FIG. 1 shows the neutralizing capacity (Schaubs Method) of the new Antacid HF product as prepared in Example 5 and compared to that of the product prepared in Example 1. The Al/Mg-ratio of Example 1 is 0.7:1 the ratio of Example 5 is 0.57:1.

After removal of the readily water-soluble components, a product can be obtained with the following properties:

1. The atomic ratio of aluminum to magnesium is from 0.5:1 to 7:1 and preferably from 1:1 to 6:1.
2. The pH value of an aqueous suspension thereof is from 5.5 to 9.0 and preferably from 6.0 to 8.5.
3. A dose of the product prepared according to the present invention with 20 mMol aluminum reaches, in the case of the determination of the acid-binding capacity by Schaub's method (see Pharm. Acta Helv., 38, 16/1963), a pH value of 3.5 after only 1 minute; in most cases, the pH value does not exceed 4.5 and, in spite of the addition of Schaub's simulated gastric juice, it remains above pH 3.0 for at least 120 minutes and, in many cases, for up to 160 minutes.
4. The active material obtained only contains the physiologically compatible cations present in the starting materials and, as anions, only contains sulfate and releases hydroxyl ions and is, therefrom, also suitable for high-dosage antacid therapy.

Thus, according to the present invention, it is possible, with very simple means and without the use of foreign additives, to prepare a highly effective antacid material which, according to present day knowledge, displays an ideal activity profile. In particular, it possesses the following properties which are demanded of an ideal antacid and is, therefore, superior to the known antacids:

1. The action commences immediately without an increased gastric acid secretion and a rebound effect resulting due to exceeding the admissible limit of pH 5.
2. The buffering of the gastric juice within the narrow ideal range of from pH 3 to pH 5 is maintained for at least 2 hours.
3. The antacid reduces the pepsin activity without, however, completely inhibiting it.
4. The antacid does not have any harmful side effects since the magnesium and aluminum ions are in a balanced ratio to one another and no undesired foreign cations, such as sodium, calcium, ammonium, bismuth and the like, and no undesired anions, such as chloride, carbonate and the like, are present.
5. The antacid also binds bile acids which play a part in the genesis of hemorrhagic gastritis and of ulcers.
6. The active material is stable, also retains its buffer capacity in dry form for a long time and has a completely neutral taste.
7. A safe preservation for the avoidance of microbial growth is possible in suspensions of this antacid material because of its optimum pH range.
8. In contradistinction to known gels, the antacid is obtained in the form of a powder which can be easily filtered or centrifuged and can also be very readily further worked up.

The process of preparation according to the present invention gives a new kind of compounds in which the strong basicity of the magnesium hydroxide or oxide component is no more present.

This leads to a previously unachieved flattening of the pH curve of the gastric juice which, in the case of the known hydroxide mixtures, always displays, shortly after administration, a distinct maximum above pH 5 but, in the present case, proceeds very flatly below pH 5.

It must be observed that the ideal atomic ratio of aluminum to magnesium depends upon the starting materials. In the case of too great an excess of aluminum salt, the magnesium hydroxide can be completely dissolved; the yield of antacid material is then at least small and such a fine precipitate is formed that separation thereof becomes difficult. In the case of too great an excess of magnesium hydroxide or oxide, a precipitate is admittedly obtained which can be easily separated but the product then assumes more and more the undesired properties of pure magnesium hydroxide and the kinetics of the acid-binding capacity (according to Schaub) deteriorate. A the commencement of treatment with such an antacid, a pH maximum above pH 5 then distinctly occurs, which is typical for magnesium hydroxide or oxide.

The atomic ratio in the antacid end product is determined by the quantitative atomic ratio of aluminum to magnesium in the starting materials. By the choice of a particular atomic ratio, it is very easy to adjust an atomic ratio of aluminum to magnesium in the antacid end product within the preferred range of from 0.5:1 to 7:1. The particle size of the magnesium hydroxide or magnesium oxide used as starting material is preferably from 10 to 100 µm.

The amounts of water used also have an influence upon the physical properties of the antacid product. In this regard, care should be taken that the concentration of the aluminum sulfate solution and of the magnesium hydroxide or oxide suspension is not too high since the product can otherwise only be filtered off with difficulty. It is preferred to use a 0.2 to 1.5 molar aqueous aluminum sulfate solution and an approximately 0.5 to 5, most preferably 0.5–1 molar magnesium hydroxide suspension as starting materials.

For the process of preparation, it is immaterial whether the aluminum sulfate in solution is added to a slurry of the magnesium hydroxide or magnesium oxide or whether the reverse procedure is used and the magnesium hydroxide or oxide slurry is introduced into the solution of the aluminum sulfate, or whether the materials in their respective solutions are added simultaneously. However, it is important continuously to monitor the pH value of the reaction mixture after mixing the reaction components together and to stir the mixture until the desired pH value has been obtained.

Since the aluminum content in the end product increases with an increasing period of stirring at the expense of the magnesium content, it is also possible to control the mole ratio to a certain extent by the period of reaction. The acidic pH value in the reaction mixture initially increases very quickly and then asymptomatically approaches the end value. For an appropriate quality of the antacid material, the components should be reacted together at least until a pH of from 4 to 8 is reached. The reaction can be accelerated by increasing the temperature, without changing the end product. However, the temperature should not exceed 60° C.

At the end of the reaction, water-soluble magnesium salts can be very easily removed by washing out. Even after a single washing of the filtered off antacid material, less than 2% of the dissolved materials (referred to the dried product) are present in the first wash water. The soluble and non-toxic salts are thus removed from the antacid material to such an extent that this can be used directly.

In practice, the product is washed twice at most. The sulfate content of the pure antacid product, dried for 4 hours at 110° C. is in the range of from 5 to 25% and preferably of from 10 to 20%.

For the determination of the optimum molar atomic ratio (i.e. in the end product, the longest possible buffering time above pH 3.0 and no increase of the pH value above 5.0 in the case of determining the acid-binding capacity by Schaub's method) of magnesium to aluminum in the starting materials, a series of experiments is carried out. The same amounts of magnesium hydroxide are thereby reacted with increasing amounts of aluminum sulfate under otherwise the same reaction conditions.

The following Table summarizes the results of this series of experiments. The experiments were carried out as follows:

2 g magnesium hydroxide were suspended in 18 g of water. Aluminum sulfate octadecahydrate was weighed out in a molar ratio and dissolved in sufficient water to give 80 g of solution. The solution was then added, with stirring, to the magnesium hydroxide suspension. The reaction mixture was stirred for 3 hours, during which time the pH value of the reaction mixture was continuously measured. The precipitate obtained was filtered off through a G3 frit under reduced pressure and well washed twice with 50 ml amounts of water. Subsequently, the product was well dried by passing air therethrough. Finally, the antacid product obtained in this manner was examined for its acid-binding capacity by Schaub's method (Pharm. Acta Helv., 38, 16/1963). The results of the experiments are given in the following Table:

TABLE

Experimental series of $Mg(OH)_2$ with $Al_2(SO_4)_3 \cdot 18H_2O$

| Atomic Ratio Mg:Al in the Starting Materials | pH Vale of the Reaction Mixture at the End of the Reaction | Yield After Drying 110° C./4 hr | Acid-Binding Capacity | |
|---|---|---|---|---|
| | | | Buffering Time Above pH 3.0 | pH Value Peak After 20 min |
| 1 Mg:0.60 Al | 6.0 | 2.18 g | 140 min | 5.1 |
| 1 Mg:0.65 Al | 6.0 | 2.59 g | 150 min | 5.0 |
| 1 Mg:0.70 Al | 5.7 | 2.67 g | 150 min | 4.1 |
| 1 Mg:0.75 Al | 5.4 | 2.78 g | 150 min | 3.9 |
| 1 Mg:0.80 Al | 4.2 | 3.05 g | 160 min | 3.6 |
| 1 Mg:0.85 Al | 4.0 | 2.50 g | 120 min | 3.8 |

The atomic ratio was calculated as follows:

2 g $Mg(OH)_2$ = 0.03429 mol Mg
8 g $Al_2(SO_4)_3 \cdot 18H_2O$ = 0.01200 mol $Al_2(SO_4)_3 \cdot 18H_2O$ = 0.02400 mol Al which corresponds to an atomic ratio in the starting materials of magnesium to aluminum of 1 0.7.

If the amounts of aluminum sulfate are too low, the disadvantageous properties of magnesium hydroxide with regard to acid-binding capacity occur, i.e. the pH value peak is above 5.0.

If the amount of aluminum sulfate is too great, the magnesium hydroxide can be completely dissolved and the precipitate is present as a gel, which is difficult to filter, or, in extreme cases, only a clear solution is obtained.

The most favorable atomic ratio can be easily determined by evaluation of the values for yield, buffering time and pH value peak. Those atomic ratios are selected within the preferred pH range (pH value peak) with which, in the case of the most favorable yields, there is associated the longest buffering time.

Gel-like aluminum or magnesium hydroxides prepared by precipitation are, because of their structure extremely difficult to filter. Surprisingly, we have found that the process according to the present invention does not suffer from this disadvantage and, especially in the preferred process ranges, gives a product which is excellent to filter and is capable of elution. This is a further considerable technical advantage over the prior art.

Using the above described process and an atomic ratio of aluminum to magnesium in the starting material of 1:1 to 1:2 and, especially, 1:1.8, a preferred antacid material, hereafter known as Antacid HF, is obtained. Antacid HF is an antacid material of the formula $[Mg_5Al_{10}(OH)_{26}O_5](SO_4)_2 \cdot nH_2O$, wherein n may vary from 35-95, preferably from 45-85, or, more preferably from 55-65 depending on the amount of drying needed. A particular embodiment has been obtained with the precise formula $[Mg_5Al_{10}(OH)_{26}O_5](SO_4)_2 \cdot 63H_2O$. Precise chemical analysis of this Antacid HF material confirms that it is a one phase entity and not a mixture of $Al(OH)_3$ and $Mg(OH)_2$. X-ray diffraction studies show no $Al(OH)_3$ and no lines for the starting materials. The structure of the Antacid HF is considered as a structure of layers, e.g., a double-layer in which cationic

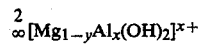

layers of the $Mg(OH)_2$ type alternate with anionic

layers. Water molecules and additional sulfate ions are deposited between these layers.

The Antacid HF product possesses all of the desirable properties. The product has excellent, long acting acid binding potential and a fast onset of action. The absence of sodium, calcium, and carbonate ions is particularly advantageous. Side effects are thus minimized. In addition, the neutralizing capacity of this product has been measured according to the procedure described in Med. Klin. 72, 1229 (1977) and The New England J. of Med. 288, No. 18, 923 (1973). In FIG. 1 the neutralizing capacity of this new product, as prepared in Example 5, is compared with the neutralizing capacity of the material of Example 1. It is evident that the new product exhibits an almost ideal neutralization curve, which is better than the neutralization curve of any other product as tested in the above-mentioned publications.

Figure 5:
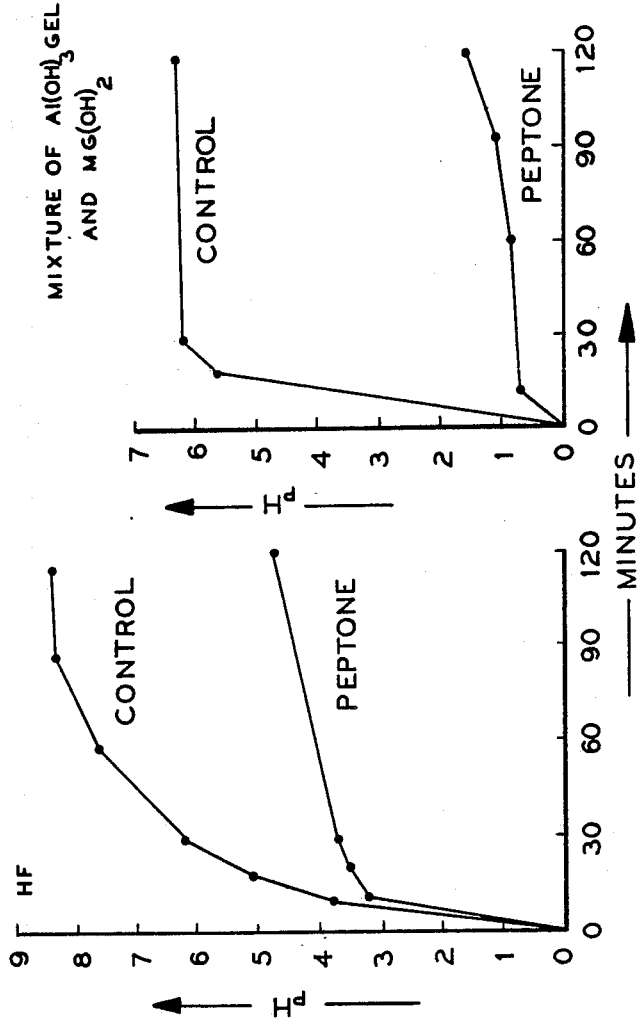
FIG. 5 illustrates the acid-neutralizing capacity of Antacid HF (product of Example 5) in the presence of control and in the presence of 5% peptone to simulate postprandial gastric juice and that of a comparison mixture.

Furthermore, in comparison to a mixture of Al-hydroxide gel and Mg-hydroxide, the Antacid HF material according to the present invention shows much better behavior in the postprandial gastric juice and in the gastric juice of the fasted stomach. The in vitro investigation according to C. Walther et al. in Z. Gastroenterologie 20 (1982) 263-272 simulates the postprandial gastric juice with the addition of peptone (FIG. 5) and the gastric juice of the fasted stomach with the addition of glutamic acid (FIG. 6).

The Antacid HF product is normally not isolated as a granulate but is combined during the manufacturing process with up to 40% of polyols, such as hexitols, for example, mannitol or sorbitol.

The process of manufacture of the Antacid HF granulate and finished product in dosage form is best carried out by the following method. For the manufacture of the HF-Granulate, an aqueous Al-sulfate solution and an aqueous Mg-hydroxide suspension are mixed intensively in-line using a static mixer and a homogenizer on the rotor-stator principle, then stirred for at least six hours. The precipitation is removed from the mother liquor by means of centrifugation with an integrated washing process.

This procedure allows use of $Mg(OH)_2$ of varying particle size, simplifies the adjustment of the process during scale up and permits shortening of the reaction time. By using a plough centrifuge, the wet cake is in a fully automated process washed and subsequently loaded with sorbitol, before emptying the centrifuge with the help of the plough. This delivers a freely flowing wet granulate which is in a following step dried to a predetermined value of relative humidity in the exhaust air in a fluidized bed drier. The material thus obtained can be directly processed into liquid or solid dosage forms.

The quantity of the sorbitol to be added can be defined by volume and concentration of the sorbitol solution used in the combined washing process.

Loading with sorbitol during the washing process can be so controlled that a sorbitol content of 29% (26%-32%) is attained in the dried granulate.

The whole process can easily be run automatically and requires one employee only for handling and supervision.

The antacid product according to the present invention can, after gentle drying, be worked up directly in known manner to give solid compositions for oral administration, for example capsules, dragees, granulates or, preferably, tablets. For the production of solid compositions for oral administration, use is made, in the conventional manner, of adjuvant and carrier materials, for example starch, lactose, mannitol, methyl cellulose, talc, highly dispersed silicic acids, high molecular weight fatty acids (for example stearic acid) and the salts or esters thereof, gelatine, agar-agar, animal and vegetable fats and solid high molecular weight polymers (for example polyethylene glycol). If desired, the compositions can also additionally contain flavoring and/or sweetening agents. The composition is preferably so dosed that one dosage unit contains 0.3 to 5.0 g of antacid product. One to two units of this composition can be administered several times a day at intervals of one to two hours.

The antacid product according to the present invention is, in a moist or dry state, also outstandingly useful for the production of suspensions, in which case, in addition to the above-mentioned adjuvants, thickening agents and conventional suspension stabilizers are also added. Suspensions are generally the preferred form of administration for antacids, for which reason they are also especially preferred according to the present invention.

The liquid forms of administration can contain, per milliliter up to 60 % (g/g) of antacid product. There are thus obtained dosage units of about 5 ml, which correspond to 50 ml milliequivalents per one teaspoonful. Here, too, depending upon the severity of the disease picture, one to two dosage units can be administered at intervals of one to two hours during the course of the day.

The antacid product according to the present invention can also be worked up in a moist state as a liquid pharmaceutical form so that drying measures can be omitted.

The active material may also be incorporated into semisolid and liquid dosage forms, such as suspensions with lower and higher viscosities, or pastes.

For the production of solid pharmaceutical forms, a gentle drying process should be used, i.e. the thermal stressing should be as small as possible.

The following Examples are given for the purpose of illustrating the present invention.

EXAMPLE 1

0.012 mol Aluminum sulfate with variable amounts of water of crystallization are dissolved, while stirring in 42 ml of water, with gentle heating up to about 50° C. 0.034 mol magnesium hydroxide, suspended in 30 ml of water, are slowly added, with vigorous stirring, to the aluminum sulfate solution. After complete addition of the suspension, the reaction mixture is stirred (about 1 hour) until the aqueous suspension has reached a pH value of 5.5. The mixture is then filtered under reduced pressure through a G3 frit and, with resuspension, washed twice with 50 ml amounts of water. After filtering off, the precipitate is dried, first at ambient temperature and then for 4 hours at 60° C. The yield is 3.0 g. The pH value of an aqueous suspension of the product is 6.0.

Composition: 0.02 mol aluminum, 0.005 mol magnesium

Acid-binding capacity by Schaub's method: buffering time (above pH 3.0) =150 minutes pH value after 20 minutes =4.1

Figure 2:
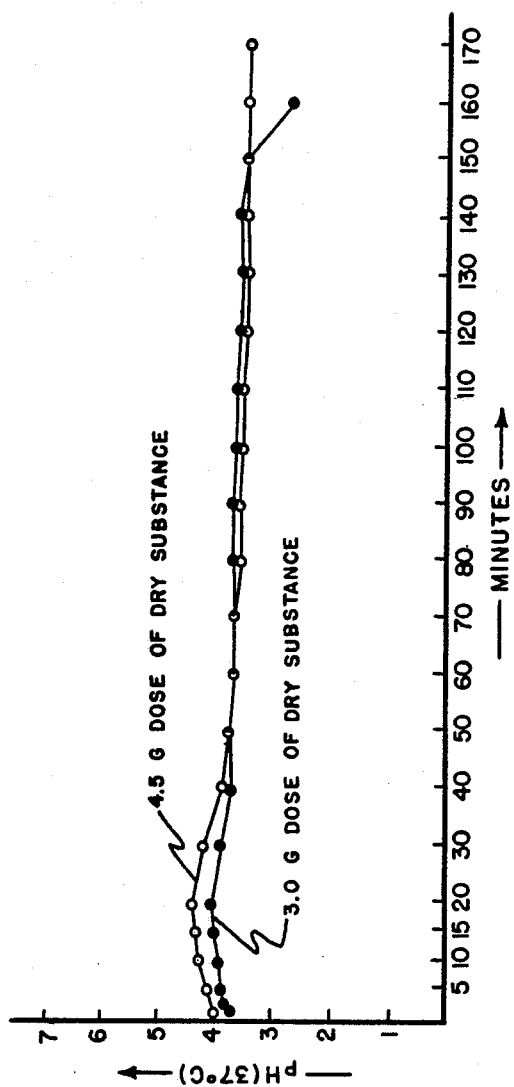
FIG. 2 to 4 illustrate the acid-binding capacities of the product of Example 1 and of a comparison mixture consisting of 0.02 mol Al (OH)$_3$ in freshly precipitated form and 0.005 mol Mg (OH)$_2$. This is an equivalent amount of Al and Mg to the composition of Example 1.
Figure 3:
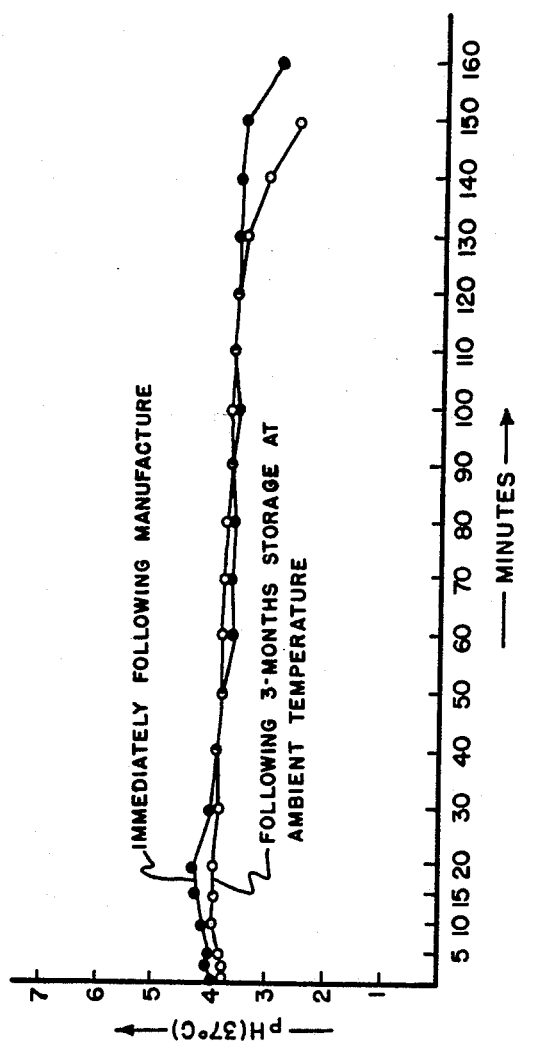
Figure 4:
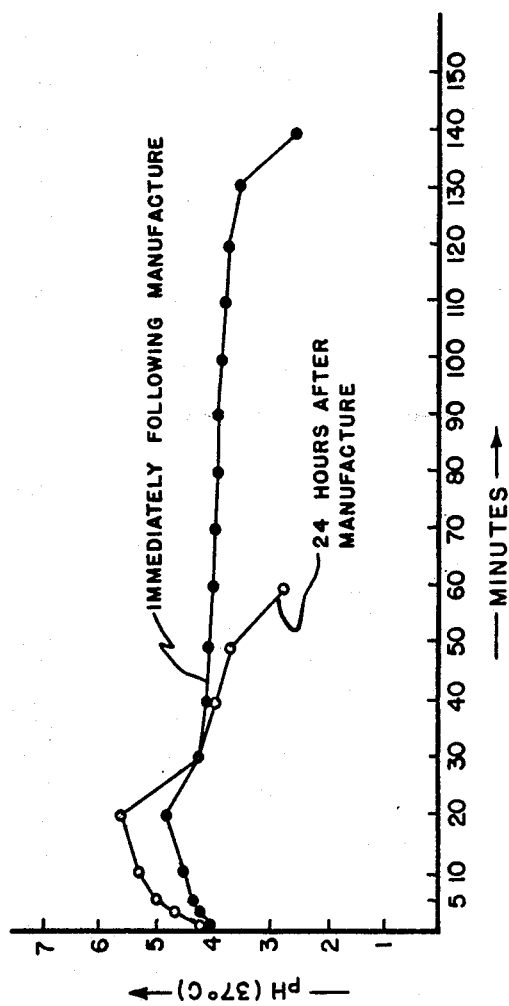

The course of the acid-binding capacity under different conditions is given in FIGS. 2 and 3 of the accompanying drawings.

EXAMPLE 2

1 kg Magnesium hydroxide is suspended in 14 kg of water. To this suspension is added a solution, prepared at 60° C. of 4 kg aluminum sulfate octadecahydrate in 21 liters of water, while stirring. After stirring for 3 hours, the reaction mixture has a pH of 5.8. The reaction mixture is then filtered off under reduced pressure and washed twice, with resuspension, with 15 liter amounts of water and dried in the air. Yield 3.5 kg.

EXAMPLE 3

223 g Aluminum sulfate octadecahydrate are dissolved in 750 g of water. Subsequently, 60 g magnesium hydroxide in pulverized form are sprinkled in, while stirring. Stirring is continued until the reaction mixture has a pH value of 4.7. The precipitate is filtered off under reduced pressure through a G3 glass frit, then well washed twice with about 200 ml amounts of water and subsequently dried by passing through air. The yield is about 480 g.

EXAMPLE 4

39 g Magnesium oxide are suspended in 0.5 liters of water. At the same time, 240 g aluminum sulfate octadecahydrate are dissolved in 0.7 liters of water and subsequently added, while stirring, to the magnesium oxide suspension. The mixture is stirred until a pH value of 4.3 is reached. After washing twice with 200 ml amounts of water, the product is filtered off and dried at 30° C. The yield is 300 g.

EXAMPLE 5

$[Mg_5Al_{10}(OH)_{26}O_5](SO_4)_2 \cdot 63H_2O$

Process of manufacture:

5.000 g Magnesium hydroxide were suspended under vigorous stirring in 143.727 g water.

16.250 g Aluminum sulfate $[Al_2(SO_4)_3 \cdot 18H_2O]$ were mixed with water to give 31.273 g of a clear solution, which is added to the magnesium hydroxide suspension. The reaction mixture is then stirred for 24 hours until the pH is adjusted to about 7.5. The reaction mixture is subsequently transferred into a centrifuge and after separation the separated solid material is washed with 30.000 g water and dried by centrifuging for another ten minutes.

| Analysis: The product obtained has been analyzed as follows: | | |
|---|---|---|
| | Calculated | Found |
| Magnesium (Mg) | 5.35% | 5.7% |
| Aluminum (Al) | 11.88% | 12.3% |
| Sulfate (SO$_4$) | 8.46% | 8.5% |
| Loss of weight by drying: | | |
| 20° C. | 50% | (63 H$_2$O) |
| 105° C. | 52% | (66 H$_2$O) |
| 140° C. | 58% | (73 H$_2$O) |
| 300° C. | 60% | (76 H$_2$O) |
| 750° C. | 68.5% | (63 H$_2$O + 2 SO$_3$) |
| Annealing residue: | | |
| | Calculated | Found |
| MgAl$_2$O$_4$ | 31.3% | 31.5% |

X-Ray diffraction diagrams do not show the reflection patterns of the hydroxides of magnesium and aluminum (brucit, gibbsit, hydrargillit).

The reflection pattern of synthetic hydrotalkit $[Mg_6Al_2(OH)_{16}]CO_3 4H_2O$ cannot be found either.

The new substance should therefore be formulated as a hydrate of an oxide-hydroxide. (Pentamagnesium-dekaaluminum-pentaoxohexaeikosihydroxide-bis (sulfate - hydrate.)

The water content is, however, variable and it is extremely difficult to allocate the water molecules to those which are chemically bound to aluminum atoms and those which are merely caged between structural layers or bound as absorptive water.

The formula $[Mg_5Al_{10}(OH)_{26}O_5](SO_4)_2 \cdot n\ H_2O$ is in line with the loss of water at low temperatures, because such processes are well known from hydroxoaluminates.

The product obtained is a white, odorless, humid but well flowing powder of neutral taste.

EXAMPLE 6

The product of Example 5 has been prepared on a manufacturing scale as follows:

5.0 Kg of magnesium hydroxide were suspended in 143.73 kg of water. Separately, a clear aqueous solution containing 8.3 kg of an hydrous aluminum sulfate $[Al_2(SO_4)_3]$ was prepared resulting in a total solution weight of 31.27 kg.

Both the above suspension and clear solution were added by separate lines connected to a rotor-stator for in-line mixing before adding the mixture into an open-vessel equipped with a stirrer. The reaction mixture was then stirred for approximately 24 hours. The pH of the reaction mixture rose during the addition from approximately 3.5 to 7.5 where it leveled off. The reaction mixture was then passed through a centrifuge. The resulting cake was washed with 20 kg of water followed by a 45% aqueous solution of sorbitol (containing 10 kg sorbitol). The cake was dried on the centrifuge for two minutes to afford 16 kg of wet Antacid HF.

The wet cake was then dried in a fluidized bed drier for 45 minutes at a temperature of 70° C. for ingoing air, 25° C. for outgoing air and where the temperature of the product was 30° C. This gave a yield of 9 kg Antacid HF granulate.

We claim:

1. An antacid material of the formula $$Mg_5Al_{10}(OH)_{26}O_5](SO_4)_2 \cdot nH_2O$$

wherein n is 35–95.

2. An antacid material according to claim 1, wherein n is 45–85.

3. An antacid material according to claim 1, wherein n is 55–65.

4. An antacid material according to claim 1 and of the formula $[Mg_5Al_{10} OH)_{26}O_5](SO_4)_2 \cdot 63H_2O$.

5. An antacid pharmaceutical composition consisting essentially of an effective amount of an antacid material according to claim 1 in admixture with a polyol.

6. A composition according to claim 5, wherein the polyol is a hexitol.

7. A composition according to claim 6, wherein the hexitol is mannitol or sorbitol.

8. A composition according to claim 5 in the form of a solid dosage unit.

9. A composition according to claim 8, wherein each solid dosage unit contains 0.3 to 5.0 g of the antacid material.

10. A composition according to claim 5 in the form of a semi solid or liquid form.

11. A composition according to claim 10, wherein the suspension contains 0.1 to 0.6 of antacid per gram material.

12. An antacid pharmaceutical composition consisting essentially of an effective amount of an antacid material according to claim 4 in admixture with up to 50% sorbitol.

13. A method of treating hyperacidity and gastrointestinal diseases which comprise administering to a mammal suffering therefrom an effective amount of an antacid pharmaceutical composition according to claim 5.

14. A method of treating hyperacidity and gastrointestinal diseases which comprises administering to a mammal suffering therefrom an effective amount of an antacid pharmaceutical composition according to claim 12.

* * * * *